United States Patent [19]
Jacobson et al.

[11] Patent Number: 6,120,666
[45] Date of Patent: Sep. 19, 2000

[54] MICROFABRICATED DEVICE AND METHOD FOR MULTIPLEXED ELECTROKINETIC FOCUSING OF FLUID STREAMS AND A TRANSPORT CYTOMETRY METHOD USING SAME

[75] Inventors: Stephen C. Jacobson; J. Michael Ramsey, both of Knoxville, Tenn.

[73] Assignee: UT-Battelle, LLC, Oak Ridge, Tenn.

[21] Appl. No.: 09/098,178

[22] Filed: Jun. 16, 1998

Related U.S. Application Data

[63] Continuation-in-part of application No. 08/721,264, Sep. 26, 1996.
[51] Int. Cl.[7] .......................... G01N 27/26; G01N 27/447
[52] U.S. Cl. ......................... 204/452; 204/450; 204/451; 204/600; 204/601; 204/603; 422/68.1; 137/807; 435/288.4; 435/288.5
[58] Field of Search ................................. 204/450, 451, 204/452, 453, 454, 455, 600, 601, 602, 603, 604, 605; 422/100, 68.1, 81; 137/597, 594, 816, 818, 825, 806, 807; 73/863, 864.15; 222/564; 435/287.1, 287.2, 287.3, 288.4, 288.5, 288.6; 436/180

[56] References Cited

U.S. PATENT DOCUMENTS 5,858,187 1/1999 Ramsey et al. ........................ 204/451

*Primary Examiner*—Jill Warden
*Assistant Examiner*—John S. Starsiak
*Attorney, Agent, or Firm*—Dann, Dorfman, Herrell and Skillman, P.C.

[57] ABSTRACT

A microfabricated device and method for electrokinetic transport of a liquid phase biological or chemical material is described. In accordance with one aspect of the present invention there is provided a microchip that is adapted for the simultaneous spatial confinement of electrokinetically driven fluidic material streams on a substrate. The apparatus includes a focusing chamber formed in a surface of the substrate and in fluid communication with two sample fluid channels and three focusing fluid channels. The device further includes electromotive means operatively connected to the sources of the sample fluid and the source of focusing fluid for electrokinetically driving the respective streams of the sample and focusing fluids through the respective channels into the focusing chamber such that the focusing fluid streams spatially confine the first and second sample fluid streams within the focusing chamber. In accordance with another aspect of this invention, there is provided a cytometry method for analyzing microscopic particles in a fluid medium on a microchip by utilizing the focusing function of the microchip. In the disclosed cytometry process the width of the fluid stream is narrowed in the focusing chamber. The microscopic particles in the focused sample fluid are then detected and/or measured using light scattering or other techniques.

23 Claims, 5 Drawing Sheets

MICROFABRICATED DEVICE AND METHOD FOR MULTIPLEXED ELECTROKINETIC FOCUSING OF FLUID STREAMS AND A TRANSPORT CYTOMETRY METHOD USING SAME

This application is a continuation-in-part of application Ser. No. 08/721,264 filed on Sep. 26, 1996, the disclosure of which is incorporated herein by reference.

This invention was made with government support under contract DE-AC05-96OR22464 awarded by the U.S. Department of Energy to Lockheed Martin Energy Research Corp. and the government has certain rights in this invention.

FIELD OF THE INVENTION

This invention relates to microfabricated designs for the electrokinetic manipulation of fluidic chemical and biological materials. More specifically, this invention provides a microchip device for spatially confining two or more sample material streams simultaneously by way of electrokinetic forces and a demonstration of transport cytometry.

BACKGROUND OF THE INVENTION

In order to facilitate the development of the biological and chemical sciences, fluidic microchip technologies are increasingly utilized to perform traditional chemical laboratory functions within a controlled microfabricated environment. Microfabricated chemical instrumentation, also know as lab-on-a-chip technology, requires the development of a plurality of microfabricated functional elements or unit processes cooperatively linked on the microchip to perform small volume chemical and biochemical measurements.

Presently, these "on-chip" laboratories facilitate the precise transport and analysis of fluidic chemical and biological materials. Microchips are characterized by reduced analysis time and reagent consumption, ease of automation, and valveless fluid control of sub-nanoliter volumes. A variety of electrically driven separations have been performed within microchannel networks. Microchips have also been developed for controlling chemical reactions, including arrays for solid-phase chemistry, reaction wells for polymerase chain reactions, channels with immobilized enzymes for transport injection analysis, and manifolds for homogenous enzyme assays.

The ability to design and machine channel manifolds with low-volume connections renders microchips suitable for combining several steps of an analytical process on one device. Microchips that combine chemical reactions with the speed of microscale CE analysis have been demonstrated for pre- and post-separation reactions, for DNA restriction digests with fragment sizing, and for cell lysis, multiplex PCR amplification and electrophoretic sizing.

Electrokinetic techniques, i.e., electroosmotically induced fluid transport and/or electrophoretic migration of ions, are the preferred methods of manipulating biological and chemical materials on microchip devices. The mixing of two or more liquid-phase materials or the dispensing of a reagent material on a microchip is accomplished by controlling the electric potentials applied to the various reservoirs to electrokinetically drive the materials housed therein through the channels of the microchip. Electrophoresis transports charged species, whereas electroosmosis imparts a velocity to all ions and neutral species. Under conditions where both electroosmosis and electrophoresis are operative, the net velocity of an ion will be the vector sum of the electroosmotic and electrophoretic velocities.

Electrokinetic transport mechanisms are highly effective for demonstrating a number of highly useful experiments as identified above. Several applications require the ability to spatially confine a sample material stream with consistent reproducibility. This spatial confinement or "electrokinetic focusing" refers to the use of electrokinetic transport to confine spatially the transport of both fluids and ions. An example of such focusing is disclosed in related co-pending application Ser. No. 08/721,264, filed Sep. 26, 1996, which describes and shows a microfabricated device and method for spatially confining a sample stream.

More recently, a need has arisen for an improved microchip wherein a plurality of microfluidic sample streams can be electrokinetically focused simultaneously and a need has been identified for efficiently analyzing microscopic particles in a fluid stream.

SUMMARY OF THE INVENTION

In accordance with one aspect of the present invention there is provided a fluidic microchip that is adapted for the simultaneous spatial confinement of electrokinetically driven fluidic material streams on a substrate. The apparatus includes a focusing chamber formed in a surface of the substrate and two sample channels formed in the surface of said substrate for carrying sample fluid streams therethrough. The device also includes three focusing channels formed in the surface of said substrate for carrying focusing fluid streams therethrough. The sample channels have respective first ends in fluid communication with a source of a sample fluid and respective second ends in fluid communication with the focusing chamber. The focusing channels are formed such that one sample channel is positioned between the first and second focusing channels and the second sample channel is positioned between the second and third focusing channels. The focusing channels have respective first ends in fluid communication with a source of focusing fluid and respective second ends in fluid communication with the focusing chamber. The apparatus further includes electromotive means operatively connected to the sources of the sample fluid and the source of focusing fluid for electrokinetically driving the respective streams of the sample and focusing fluids through the respective channels into said focusing chamber such that the focusing fluid streams spatially confine the first and second sample fluid streams within the focusing chamber.

In accordance with another aspect of this invention, there is provided a method for analyzing microscopic particles in a fluid stream on a microchip. The method includes the step of conducting a stream of a sample fluid containing the microscopic particles through a sample fluid channel to a focusing chamber. In the process the width of the sample fluid stream is narrowed in the focusing chamber by electrokinetically transporting a focusing fluid into the focusing chamber on opposite sides of the sample fluid stream. The process includes the further step of detecting the microscopic particles in the focused sample fluid at a preselected detection zone on the microchip.

BRIEF DESCRIPTION OF THE DRAWINGS

The foregoing summary, and the following detailed description, will be better understood when read in conjunction with the attached drawings, in which.

DETAILED DESCRIPTION

The fluidic microchip according to this invention will be described in connection with two preferred embodiments thereof. In one embodiment, a focusing chamber is provided on the microchip in which two sample material streams are laterally confined or focused using a focusing fluid provided through three focusing channels. In the second embodiment, the microchip according to this invention includes collection channels for receiving the focused sample material streams and a buffer channel for providing a buffer fluid to selectively direct the transport of the focused sample material streams into the collection channels. A method of analyzing a fluidic sample material using a microchip according to this invention is also described in connection with a working example of transport cytometry.

MULTIPLEXED ELECTROKINETIC FOCUSING

A device embodying this invention uses electrokinetic forces to drive streams of fluidic materials through microfabricated channels. The microfabricated device includes multiple sample and focusing channels in fluidic communication with a focusing chamber for spatially confining the streams of fluidic materials traveling therethrough simultaneously. The focusing chamber is formed at the confluence of the sample and focusing channels that are formed in the substrate of the microchip. The sample and focusing fluid streams are electrokinetically manipulated such that the widths of the sample fluid streams can be substantially narrowed. Focusing of the sample fluid streams is achieved using electrophoresis, electroosmosis, or a combination thereof. The focusing or spatial confinement is achieved by using a fluidic buffer material that is passed to the focusing chamber through the focusing channels. The spatial confinement of the sample fluid stream passing through the focusing chamber is caused by having a greater electrokinetic field strength in the focusing fluid channels relative to the sample fluid channels.

Figure 1:
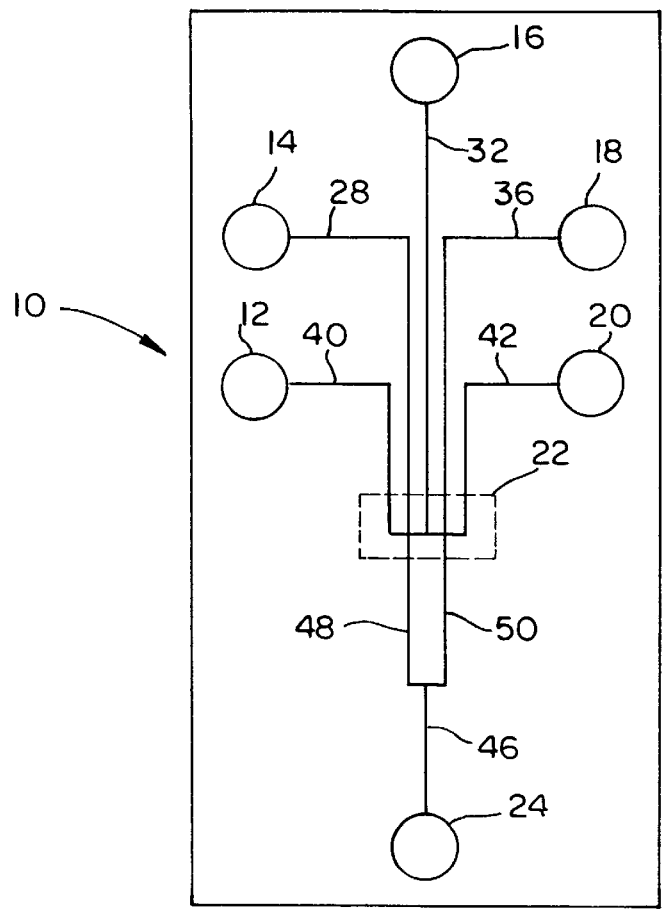
FIG. 1 is a schematic diagram of a fluidic microchip for spatially focusing sample material streams in accordance with the present invention.

Referring now to the drawings wherein like reference numerals refer to the same or similar components across the several views, and in particular to FIG. 1, there is shown a microfabricated (microchip) device 10 in accordance with the present invention. Microchip device 10 is designed and fabricated from a solid substrate material, preferably glass. However, silicon may also be used because of the well-developed technology permitting its precise and efficient fabrication. Other materials, including polymers, quartz, fused silica, sapphire, or plastics are also suitable as substrate materials. The surface of the microfabricated device 10 is covered and sealed by a cover plate.

The fluid conduction channels on microchip device 10 are formed using micromachining methods known to those skilled in the art. The micromachining methods available include film deposition processes such as spin coating and chemical vapor deposition, laser fabrication or photolithographic techniques such as UV or X-ray processes, or etching methods which may be performed by either wet chemical processes or plasma processes. Preferably, the microchannel configurations are transferred onto the substrate material using a positive photoresist, photomask, and UV exposure. The channels are etched into the substrate in a dilute, stirred $HF/NH_4F$ bath.

The microfabricated device 10 has sample channels 28 and 36, focusing channels 40, 32, and 42, and waste channels 48, 50, and 46 formed in the surface thereof. Sample reservoirs 14 and 18 are formed or positioned at the ends of the sample channels 28 and 36, respectively, such that the sample channels are in fluid communication with the respective reservoirs. Focusing reservoirs 12, 16 and 20 are similarly associated with the focusing channels 40, 32, and 42. A waste reservoir 24 is formed or positioned at the end of the waste channel 46. In the embodiment shown and described herein, the sample channels 28 and 36, the focusing channels 40, 32, and 42, and the waste channels 48, 50, and 46 each have a nominal width of 42 $\mu$m at half-depth and a nominal depth of 8.6 $\mu$m.

An electric voltage source (not shown) is connected to the various reservoirs. Electrical contact to the reservoirs is made using platinum wire to operably link the device 10 with the source of electric potential. The electroosmotic mobility for this microchip is that of native glass.

Figure 2A:
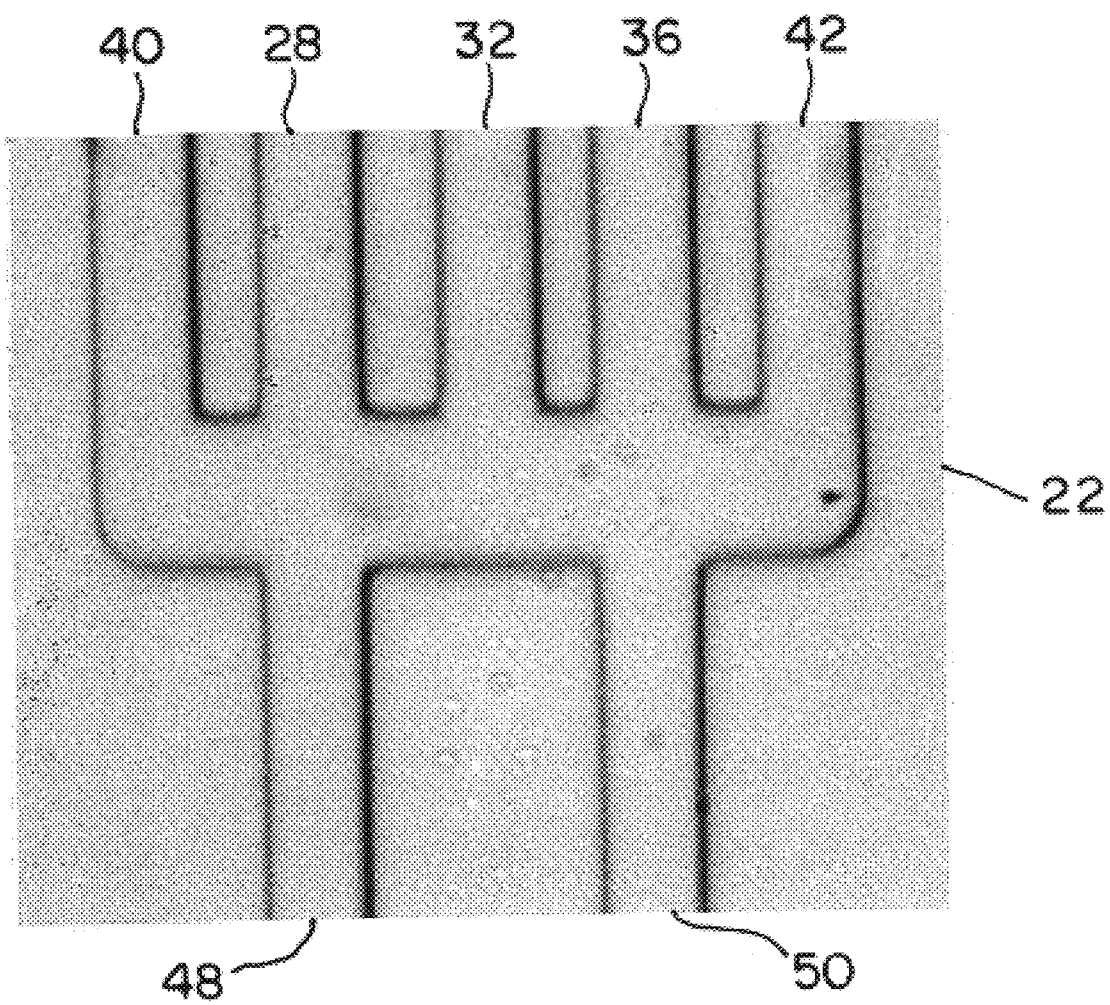
FIG. 2A is a CCD image of a focusing chamber in the fluidic microchip device shown in FIG. 1.

Referring now to FIG. 2A, a focusing chamber 22, is formed in the surface of the microchip device 10 at the confluence of sample channels 28 and 36, the focusing channels 40, 32, and 42, and the waste channels 48 and 50. In the embodiment shown, the focusing chamber has a width of about 360 $\mu$m, a length of about 71 $\mu$m, and a depth of about 8.6 $\mu$m. The channel and focusing chamber dimensions were measured using a stylus-based surface profiler and the channel widths and lengths reported were measured at half-depth.

In the microchip device 10 shown and described herein, the sample fluid is continuously infused through the focusing chamber. The electric potentials at the reservoirs are adjusted to increase or diminish the degree of lateral focusing. The potential applied at each sample and focusing reservoir is controlled independently, and the waste reservoir is grounded. Small variations in channel lengths and widths require that the voltages applied to the reservoirs differ slightly for balancing the field strengths to obtain a symmetric fluid transport in the focusing chamber. The sample field strength is defined as the electric field strength in the sample channel, and correspondingly, the focusing field strength is the electric field strength in the focusing channels. All sample stream profiles are measured at full width half maximum (fwhm) at the exit of the focusing chamber (inlet of the waste channel). Assuming that the experimental conditions, e.g., relative conductivities of the buffers, applied voltages, electroosmotic transport, remain unchanged, the variability of the stream width over time remains essentially constant.

In the microchip device 10 according to this invention, it is not necessary for the sample materials to traverse a narrow focusing chamber and transport into one or more narrow waste channels as depicted in FIG. 2A. Instead, the sample and focusing channels may terminate in a focusing chamber having a width that spans all of the sample and focusing channels. In such case the focusing chamber can be several mm or more in length. Focusing is still achieved with such an open focusing chamber design. However, spatial confinement of the sample streams is improved by about 1.6 times in a device as shown in FIG. 2A wherein the three channels converge into a single, narrower waste channel. The focused stream width is proportioned to the width of the exit of the focusing chamber (inlet of the waste channel). For example, in the embodiment shown in FIGS. 2A and 2B, the fluid streams in focusing channels 40 and 32 and sample channel 28 converge into waste channel 48, and the fluid streams in focusing channels 32 and 42 and sample channel 36 converge into waste channel 50. The narrow waste channels 48 and 50 provide a physical barrier, i.e., transport obstruction, which improves the confinement of the electrokinetic focusing. This applies to single and multiple sample electrokinetic focusing chambers. Thus, tighter lateral confinement is achieved with narrower focusing chamber and waste channels.

The multiplexed electrokinetic focusing effect provided by the microchip device 10 as described herein was observed by using laser induced fluorescence (LIF) in connection with a charge-coupled device (CCD) for imaging. An argon ion laser beam (514.5 nm, 100 mW) was expanded to approximately a 5 mm diameter at the surface of the microfabricated device 10 using a lens. The fluorescence signal was collected using an optical microscope, filtered spectrally (550 nm cut-on), and measured by the CCD. In the example operation, the buffer material used in focusing channels 40, 32, and 42 is 10 mM sodium tetraborate, and the sample channel material is rhodamine 6G (10 μM) in 10 mM buffer. The focusing effect on the sample fluid streams in sample channels 28 and 32 as they pass through the focusing chamber 22 is clearly observable in the CCD image of FIG. 2B.

Figure 2B:
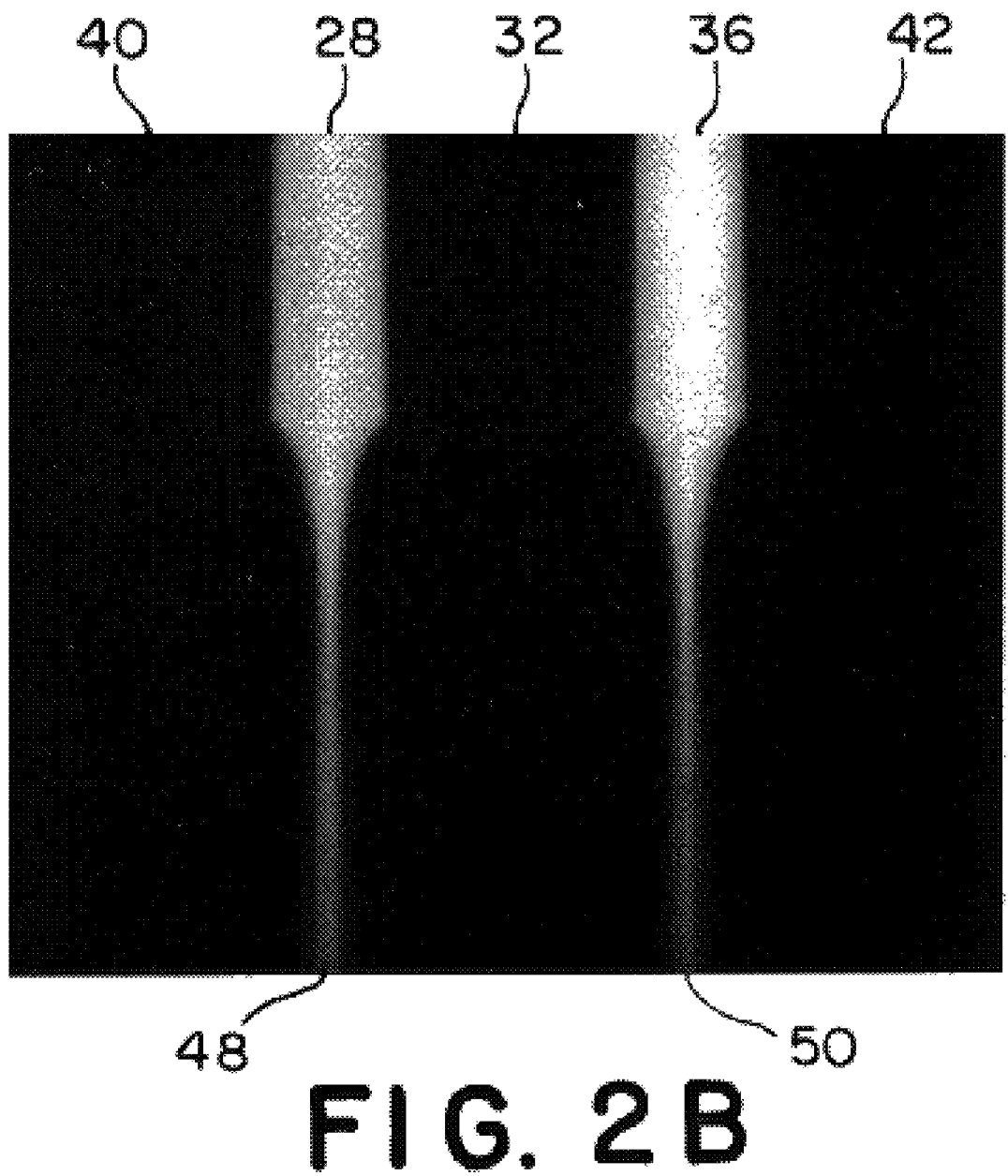
FIG. 2B is a CCD image of the simultaneous focusing of two fluidic materials in the focusing chamber of FIG. 2A.

In FIG. 2B the sample fluid streams 28 and 36 are simultaneously focused to an average width of about 8 μm using the focusing microchip 10 of FIG. 1 and 2A. The stream width is measured at the exit of the focusing chamber. The sample channels 28 and 36 have a center-to-center spacing of 160 μm. The average electric field strength in the sample channels (28 and 36) is 40 V/cm. The average field strength in the two outside focusing channels (40 and 42) is 400V/cm and the average field strength in the center focusing channel (32) is 750 V/cm. The field strength in the center focusing channel is almost twice the magnitude of the field in the outer focusing channel because the center channel must aid in focusing the sample fluid streams in channels 28 and 36. The electric potentials at each focusing reservoir (12, 16, and 20) are individually controlled in order to tune the focusing effect of the focusing fluid and achieve a symmetrically focused sample stream. Such functionality permits greater flexibility for studying transport dynamics but would not be necessary once a microchip design is finalized.

Lateral spatial confinement (focusing) of the sample material stream from sample channel 28 occurs when the transport of focusing fluid into the focusing chamber 22 from each of the focusing channels 40 and 32 is greater than the transport of sample fluid into focusing chamber 22 from sample channel 28. Likewise, lateral spatial confinement of the sample material stream in sample channel 36 occurs when the transport of focusing fluid into the focusing chamber 22 from each of the focusing channels 32 and 42 is greater than the transport of sample fluid into focusing chamber 22 from sample channel 36. If the focusing flow is too large the sample is not electrokinetically transported from the sample reservoir to the focusing chamber. The focusing channel 32 in the middle of microchip 10 confines the sample streams in the two adjacent sample channels 28 and 36, thereby limiting the total number of focusing channels needed. The multiplexed focusing provided by a microchip fabricated in accordance with the present invention can be extended to larger numbers of sample streams as necessary.

Figure 3:
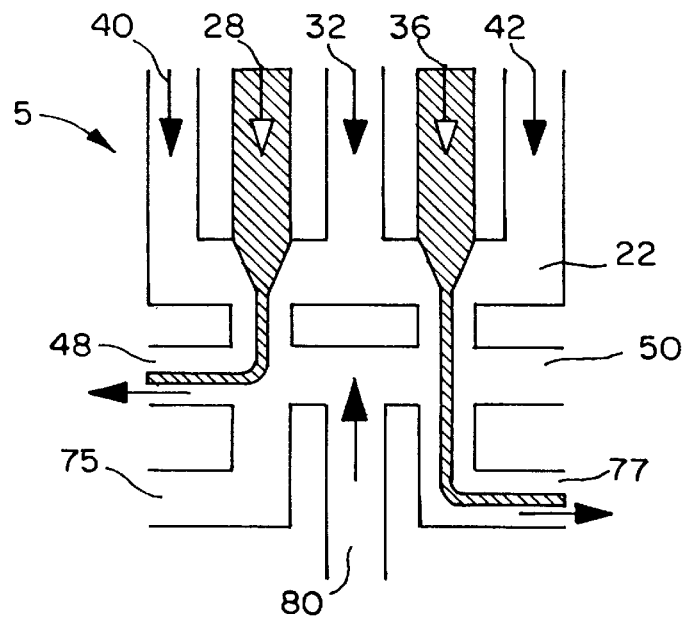
FIG. 3 is a schematic diagram of a second embodiment of a fluidic microchip in accordance with the present invention.

Shown in FIG. 3 is a second embodiment of a multiplexed, electrokinetic focusing device according to the present invention. A microchip device 5 has a focusing chamber 22, focusing channels 40, 32, and 42, sample channels 28 and 36, and waste channels 48 and 50 which are formed on a substrate in the same manner as the embodiment shown in FIGS. 1 and 2A. However, the microchip device five also has two sample collection channels 75 and 77, as well as a buffer channel 80, which are interconnected with the waste channels 48 and 50. Each of the collection channels is in fluidic communication with a collection reservoir (not shown) disposed at a remote end of the respective collection channel. In the microchip device 5, one or both of the sample streams of interest can be diverted to a collection channel after being probed at a location just downstream of the focusing chamber 22. In the embodiment shown in FIG. 3, sample fluid from sample channel 28 is directed to waste channel 48 after exiting the focusing chamber. A buffer fluid is provided through the buffer channel 80 at a transport level sufficient to prevent the focused sample fluid stream from traveling into the sample collection channel 75. Sample fluid from sample channel 36 is directed to collection channel 77 after it exits the focusing chamber 22. Such transport direction is achieved by lowering the electric potential applied to the sample collection reservoir that is in fluidic communication with sample collection channel 77. An alternative method of directing the focused sample fluid to the sample collection channel is to raise the electric potential at the waste reservoir for waste channel 50 relative to the collection reservoir for the sample collection channel 77. The sample collection channels can be operated independently or in concert with each other.

TRANSPORT CYTOMETRY

Figure 4:
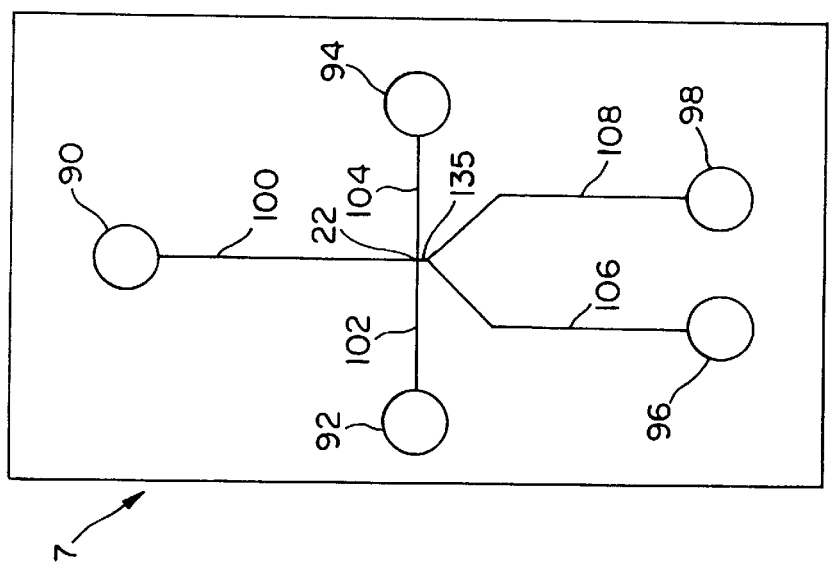
FIG. 4 is a schematic diagram of a microchip in accordance with the present invention that is used for transport cytometry of microscopic particles.

Referring now to FIG. 4, a method of performing transport cytometry is demonstrated using electrokinetic focusing of a sample fluid containing microscopic latex particles. A microfabricated device 7 includes a waste reservoir 96, focusing reservoirs 92 and 94, a sample reservoir 90, and a collection reservoir 98. A sample channel 100 is in fluid communication at one thereof with the sample reservoir 90. Focusing channels 102 and 104 are in fluid communication at first ends thereof with focusing reservoirs 92 and 94, respectively. A waste channel 106 is in fluid communication at one thereof with the waste reservoir 96 and a collection channel 108 is in fluid communication at one thereof with the collection reservoir 98. A focusing chamber 22 is formed at the confluence of the sample channel 100 and the focusing channels 102 and 104. A short channel segment 135 is provided on the downstream side of focusing chamber 22 to provide a probe region where microscopic particles in the sample fluid are analyzed. The probe region can be positioned at the exit of the focusing chamber 22 or slightly downstream of the focusing chamber 22 to minimize the scattering of the light by the channel walls. An imaging device 160 and image control processor 150 are provided for obtaining and analyzing observable information about the particles. The microchip 7 has uniform channel dimensions of 53.5 μm wide and 15.8 μm deep.

Particle detection is preferably performed with a light scattering technique, but other techniques such as fluorescence, absorbence, or refractive index could be used independently or in concert. The imaging device 160 is preferably embodied as an argon ion laser operating at a wavelength of 514.5 nm and a power of about 10 mW. The beam from the imaging device is focused to a spot approximately 50 $\mu$m on the probe region 135 located slightly downstream of the focusing chamber 22. Focusing of the laser beam is accomplished with a focusing lens having a 200 mm focal length. The light scattered by the particles in the sample fluid is collected using a 100×(0.7 NA) objective lens. The scattered light is spatially filtered and measured using a photomultiplier tube. The photomultiplier response is amplified and recorded by processing means 150, preferably a Macintosh computer with an ADC interface and running Labview 4.1, a proprietary software product of National Instruments. In a working example of the cytometry process of this invention, a buffer solution of 10 mM sodium tetraborate containing latex spheres 1.89 $\mu$m in diameter was used.

The testing was performed with continuous transport of the particles through the focusing chamber 22, and the relative potentials at the reservoirs were varied to increase or diminish the degree of focusing of the sample fluid stream so that the focused stream was approximately commensurate with the diameter of the spatial filter used in the detection apparatus. The electric potentials applied at the sample reservoir 90 and focusing reservoirs 92 and 94 were controlled independently, whereas the sample collection reservoir 98 was grounded. No electric potential was applied to the waste reservoir 96, i.e., it was allowed to float. Small variations in channel lengths and widths required that the voltages applied to the focusing reservoirs differ slightly to balance the field strengths and to obtain symmetric fluid transport into the focusing chamber.

Figure 5:
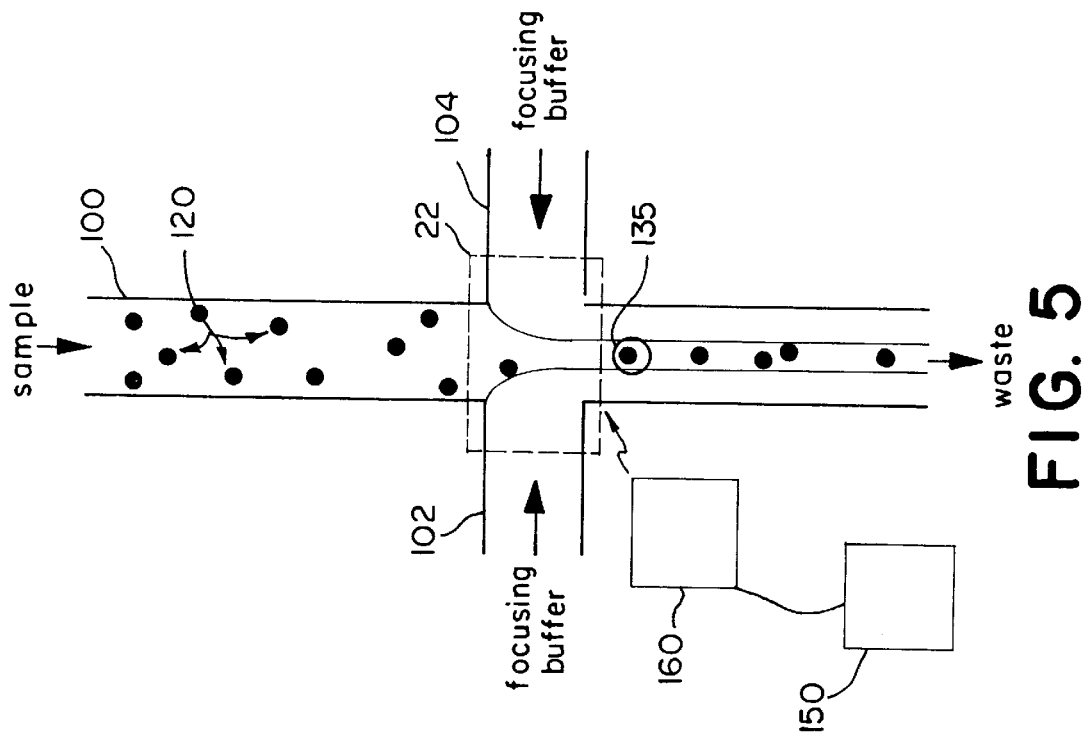
FIG. 5 is a schematic representation of the operation of a microchip according to the present showing the use of such a microchip for transport cytometry of microscopic latex particles in a fluid stream.
Figure 6:
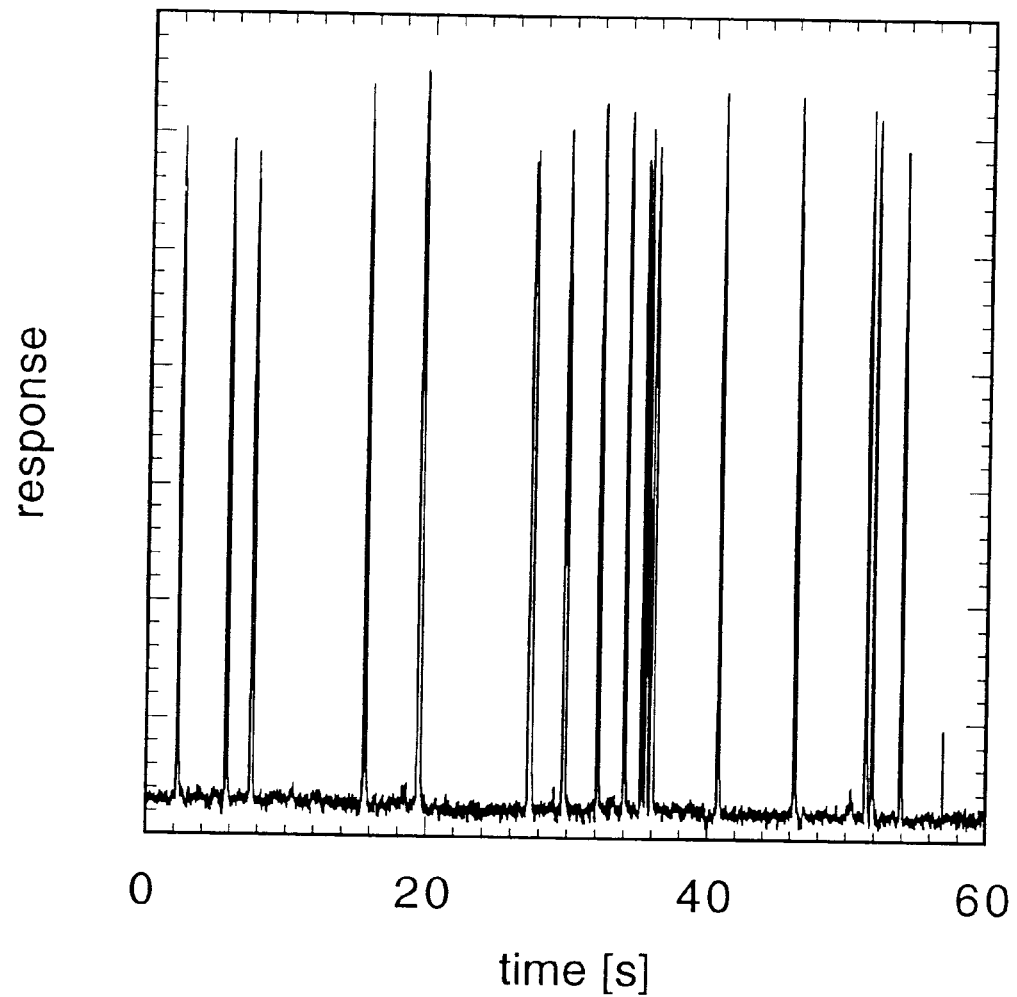
FIG. 6 is a graph of the arrival time distribution of the microscopic latex particles shown in FIG. 5 as detected at the observation zone following electrokinetic focusing and light scattering detection.

Referring now to FIG. 5, the manner in which the cytometry process according to this invention is carried out will be described. The particles 120 are transported from the sample reservoir 90 along sample channel 100. The stream of carrier fluid is transported to and confined laterally in the focusing chamber 22 as described above. The particles 120 pass through the probe region 135 and are detected using light scattering, fluorescence, or both. FIG. 6 shows the arrival time distribution of the particles 120 after being electrokinetically focused and detected in the probe region 135. The scattering intensity is nearly uniform because of the narrow distribution of particle sizes and the small variation of their lateral position resulting from the electrokinetic focusing.

By alternating the electric potentials applied to the waste reservoir 96 and the collection reservoir 98 by way of the control processor 150, the latex particles 120 can be directed to either the waste reservoir or the collection reservoir based upon fluorescent signature of the particles observed in the probe region 135. It will be appreciated that the latex particles used in the present example, can be substituted by other types of particles such as cells, bacteria, other polymeric particles, inorganic particles, environmentally collected particles, molecules, etc.

A microfabricated device in accordance with the present invention has been described. The device employs electrokinetic focusing for spatially confining at least two streams of sample materials passing therethrough. In this way, the microfabricated device is capable of processing a plurality of sample materials simultaneously. The device of the present invention is advantageous for use in various analytical procedures, including cellular analysis. The spatial confinement of the sample fluid in the focusing chamber allows high efficiency, high sensitivity fluorescence detection in a small volume and the parallel arrangement allows high sample throughput. Also, these devices can be operated with any combination of electrokinetic transport and pressure-driven flow to achieve comparable results.

The terms and expressions which have been employed are used as terms of description and not of limitation. There is no intention in the use of such terms and expressions of excluding any equivalents of the features shown and described or portions thereof. It is recognized, however, that various modifications such as channel dimension, location, and arrangement are possible within the scope of the invention as claimed.

That which is claimed is:

1. An apparatus for the simultaneous spatial confinement of material streams on a substrate, comprising:

a focusing chamber formed in a surface of the substrate;

first and second sample channels formed in the surface of said substrate for carrying sample fluid streams therethrough, said sample channels having respective first ends in fluid communication with a source of a sample fluid and respective second ends in fluid communication with said focusing chamber;

first, second, and third focusing channels formed in the surface of said substrate for carrying focusing fluid streams therethrough, said focusing channels being formed such that said first sample channel is positioned between said first and second focusing channels and said second sample channel is positioned between said second and third focusing channels, said focusing channels having respective first ends in fluid communication with a source of focusing fluid and respective second ends in fluid communication with said focusing chamber;

first and second waste channels formed in the surface of said substrate, said waste channels having respective first ends in fluid communication with said focusing chamber and having respective second ends in fluid communication with a waste reservoir; and means operatively connected to the source of the sample fluids and the source of focusing fluid for driving the respective streams of the sample and focusing fluids through the respective channels into said focusing chamber such that the focusing fluid streams spatially confine the first and second sample fluid streams within said focusing chamber.

2. An apparatus according to claim 1 further comprising:

first and second sample collection channels formed in the substrate for carrying the respective streams of the sample fluid, said sample collection channels having respective first ends in fluid communication with corresponding waste channels and having respective second ends in fluid communication with first and second collection reservoirs, respectively; and a buffer channel formed in the substrate for carrying a stream of buffer fluid, said buffer channel having a first end in fluid communication with a source of buffer fluid and a second end in fluid communication with said first and second waste channels; and means operatively connected to the source of the buffer fluid, the collection reservoir, and the waste reservoir for driving the buffer fluid through the buffer channel to direct the streams of the sample fluid to corresponding waste channels, to corresponding collection channels, or to a combination of a waste channel and a collection channel.

3. An apparatus as set forth in claim 1 wherein the respective first ends of the first and second waste channels are positioned substantially opposite the respective second ends of the first and second sample channels in said focusing chamber.

4. An apparatus as set forth in claim 1 wherein the first and second waste channels have respective widths that are narrower in dimension than the widths of the first and second sample channels, respectively.

5. An apparatus as set forth in claim 1 wherein the first and second sample channels have respective widths that are narrower in dimension than the widths of the first and second waste channels, respectively.

6. An apparatus as set forth in claim 1 wherein the widths of the sample channels and the widths of the waste channels are narrower in dimension than the widths of the focusing channels.

7. A method for analyzing microscopic particles in a fluid medium on a microchip comprising the steps of:

conducting a stream of a sample fluid containing microscopic particles through a sample fluid channel to a focusing chamber;

narrowing the width of the sample fluid stream in the focusing chamber by transporting a focusing fluid into the focusing chamber such that the width of the sample fluid stream in the focusing chamber corresponds substantially to a detection zone; and detecting the microscopic particles in the focused sample fluid in the detection zone.

8. A method as set forth in claim 7, further comprising the step of measuring a physical characteristic of the microscopic particles.

9. A method as set forth in claim 8 further comprising the steps of:

comparing the measured physical characteristic to a reference value for the physical characteristic;

diverting the sample fluid stream to a first channel when the measured physical characteristic has a first quantitative relationship to the reference value; and diverting the sample fluid stream to a second channel when the measured physical characteristic has a second quantitative relationship to the reference value.

10. A method as set forth in claim 7 wherein the step of narrowing the width of the sample fluid stream further comprises the step of narrowing the width of the sample fluid channel.

11. Apparatus for analyzing microscopic particles in a fluid medium on a microchip having a substrate, comprising:

a focusing chamber formed in a surface of the substrate;

a sample channel formed in the surface of said substrate for carrying a sample fluid stream therethrough, said sample channel having a first end in fluid communication with a source of a sample fluid containing microscopic particles and a second end in fluid communication with said focusing chamber;

first and second focusing channels formed in the surface of said substrate for carrying focusing fluid streams therethrough, said focusing channels having respective first ends in fluid communication with a source of focusing fluid and respective second ends in fluid communication with said focusing chamber;

a detection channel formed in the surface of said substrate and having a first end in fluid communication with said focusing chamber for receiving the sample fluid therefrom;

means operatively connected to the source of the sample fluid and the source of focusing fluid for driving the respective streams of the sample and focusing fluids through the respective channels into said focusing chamber such that the focusing fluid streams spatially confine the sample fluid stream within said focusing chamber and said detection channel; and means for detecting the microscopic particles in the spatially confined sample fluid in said detection channel.

12. An apparatus as set forth in claim 11 further comprising a collection channel formed in the surface of said substrate, said collection channel having a first end in fluid communication with said detection channel.

13. An apparatus as set forth in claim 12 further comprising a waste channel formed in the surface of said substrate, said waste channel having a first end in fluid communication with said detection channel.

14. An apparatus as set forth in claim 13 wherein the means for detecting the microscopic particles comprises analyzing means for measuring a physical characteristic of the microscopic particles.

15. An apparatus as set forth in claim 14 wherein the analyzing means comprises:

comparing means for comparing the measured physical characteristic to a reference value for the physical characteristic; and diverting means for diverting the sample fluid stream to the collection channel when the measured physical characteristic has a first quantitative relationship to the reference value and for diverting the sample fluid stream to the waste channel when the measured physical characteristic has a second quantitative relationship to the reference value.

16. Apparatus as set forth in claim 13 further comprising a buffer channel formed in the substrate for carrying a stream of buffer fluid, said buffer channel having a first end in fluid communication with a source of buffer fluid and a second end in fluid communication with said collection channel and said waste channel; and means operatively connected to the source of the buffer fluid, the collection channel and the waste channel for driving the buffer fluid through the buffer channel to direct the stream of the sample fluid to the waste channel, to the collection channel, or to both the waste channel and the collection channel.

17. An apparatus as set forth in claim 11 wherein the detection channel has a width that is narrower in dimension than the width of the sample channel.

18. An apparatus as set forth in claim 11 wherein the sample channel has a width that is narrower in dimension than the width of the detection channel.

19. An apparatus as set forth in claim 11 wherein the sample channel and the detection channel have respective widths that are narrower in dimension than the width of either of the focusing channels.

20. An apparatus for the spatial confinement of a material stream, comprising:

a focusing chamber formed in a surface of a substrate;

a first sample channel formed in the surface of the substrate for conducting a first sample fluid stream therethrough, said first sample channel having a first end in fluid communication with a source of a sample fluid and a second end in fluid communication with said focusing chamber;

first and second focusing channels formed in the surface of the substrate for conducting focusing fluid streams therethrough, said focusing channels having respective first ends in fluid communication with a source of focusing fluid and respective second ends in fluid communication with said focusing chamber;

a first waste channel formed in the surface of the substrate, said first waste channel having a first end in fluid communication with said focusing chamber and a second end in fluid communication with a waste reservoir; and means operatively connected to the source of the sample fluid and the source of focusing fluid for driving the respective streams of the sample and focusing fluids through the focusing and sample channels into said focusing chamber, whereby the focusing fluid streams spatially confine the first sample fluid stream within said focusing chamber.

21. An apparatus as set forth in claim 20 wherein the first sample channel has a width that is narrower in dimension than the width of either of the focusing channels.

22. An apparatus as set forth in claim 20 wherein the first waste channel has a width that is narrower in dimension than the width of either of the focusing channels.

23. An apparatus as set forth in claim 22 wherein the first sample channel has a width that is narrower in dimension than the width of either of the focusing channels.

* * * * *